(12) United States Patent
Pedlar

(10) Patent No.: US 7,857,154 B2
(45) Date of Patent: Dec. 28, 2010

(54) CONTAINER WITH LID AND TAMPER-EVIDENT FEATURES

(75) Inventor: Sharen Louise Pedlar, Cambridge (GB)

(73) Assignee: Camlab Limited, Cambridge (GB)

( * ) Notice: Subject to any disclaimer, the term of this patent is extended or adjusted under 35 U.S.C. 154(b) by 537 days.

(21) Appl. No.: 11/813,666

(22) PCT Filed: Feb. 21, 2006

(86) PCT No.: PCT/GB2006/000612

§ 371 (c)(1),
(2), (4) Date: Aug. 28, 2007

(87) PCT Pub. No.: WO2006/090137

PCT Pub. Date: Aug. 31, 2006

(65) Prior Publication Data

US 2008/0093363 A1   Apr. 24, 2008

(30) Foreign Application Priority Data

Feb. 22, 2005   (GB) ................................ 0503623.1

(51) Int. Cl.
*B65D 55/02* (2006.01)
(52) U.S. Cl. ...................... 215/256; 215/252; 215/901; 220/268; 220/276
(58) Field of Classification Search ......... 215/252–254, 215/256, 901; 220/265, 266, 268, 276
See application file for complete search history.

(56) References Cited

U.S. PATENT DOCUMENTS

| 1,908,245 | A | * | 5/1933 | Hogg | ........................... 215/252 |
|---|---|---|---|---|---|
| 3,441,161 | A | * | 4/1969 | Van Baarn | ................... 215/235 |
| 3,595,420 | A | * | 7/1971 | Miskin | ....................... 215/256 |
| 3,672,528 | A | * | 6/1972 | Faulstich | ..................... 215/256 |
| 3,837,518 | A | * | 9/1974 | Gach | .......................... 215/365 |
| 3,871,545 | A | * | 3/1975 | Bereziat | ..................... 215/249 |
| 3,901,403 | A | * | 8/1975 | Menke | ........................ 215/251 |
| 3,904,062 | A | * | 9/1975 | Grussen | ...................... 215/252 |
| 3,927,784 | A | * | 12/1975 | Cochrane | .................... 215/256 |
| 3,955,716 | A | * | 5/1976 | Goncalves | ............. 222/153.07 |
| 3,991,904 | A | * | 11/1976 | Davis et al. | ................. 215/256 |

(Continued)

FOREIGN PATENT DOCUMENTS

EP   1251076 A1   10/2002

(Continued)

*Primary Examiner*—Anthony Stashick
*Assistant Examiner*—Ned A Walker
(74) *Attorney, Agent, or Firm*—Townsend and Townsend and Crew LLP

(57) ABSTRACT

Apparatus (10) for securing sample collection, comprises an open-topped container (12), a lid (14) for securely covering the open-topped container (12) to prevent access to container contents, and first and second tamper-evident features (16, 18) each having a frangible portion (20, 22) which fractures in use to provide an indication of tampering with container contents when its respective tamper-evident feature is activated. The first and second tamper-evident features (16, 18) are independently-operable, with activation of the first tamper-evident feature (16) preventing activation of the second tamper-evident feature (18) until the frangible portion (20) of the first tamper-evident feature (16) is fractured. The second tamper evident feature (18) is operable without having to remove the fractured frangible portion (20) of the first tamper evident feature (16) from the apparatus (20).

24 Claims, 7 Drawing Sheets

U.S. PATENT DOCUMENTS

| | | | | |
|---|---|---|---|---|
| 4,032,029 A * | 6/1977 | Cochrane | ... | 215/256 |
| 4,037,746 A * | 7/1977 | Ver Hage | ... | 215/45 |
| 4,149,647 A * | 4/1979 | Ritzenhoff | ... | 215/254 |
| 4,166,552 A * | 9/1979 | Faulstich | ... | 215/256 |
| 4,231,486 A * | 11/1980 | Bock | ... | 220/266 |
| 4,305,516 A * | 12/1981 | Perne et al. | ... | 215/252 |
| 4,326,639 A * | 4/1982 | Stahl et al. | ... | 215/252 |
| 4,346,811 A * | 8/1982 | Hilaire | ... | 215/252 |
| 4,417,666 A * | 11/1983 | Roberts | ... | 215/256 |
| 4,485,934 A * | 12/1984 | Maguire | ... | 215/252 |
| 4,512,485 A * | 4/1985 | Agbay et al. | ... | 215/225 |
| 4,522,307 A * | 6/1985 | Steiner | ... | 215/219 |
| 4,530,437 A * | 7/1985 | Gray et al. | ... | 215/252 |
| 4,531,650 A * | 7/1985 | Friendship | ... | 215/256 |
| 4,534,479 A * | 8/1985 | Conti | ... | 215/252 |
| 4,540,100 A * | 9/1985 | Willis | ... | 215/252 |
| 4,557,393 A * | 12/1985 | Boik | ... | 215/253 |
| 4,562,931 A * | 1/1986 | Brach et al. | ... | 215/220 |
| 4,589,561 A * | 5/1986 | Crisci | ... | 215/256 |
| 4,593,830 A * | 6/1986 | Bullock | ... | 215/256 |
| 4,613,052 A * | 9/1986 | Gregory et al. | ... | 215/252 |
| 4,657,153 A * | 4/1987 | Hayes | ... | 215/252 |
| 4,667,839 A * | 5/1987 | Crisci | ... | 215/256 |
| 4,805,792 A * | 2/1989 | Lecinski, Jr. | ... | 215/253 |
| 4,860,907 A * | 8/1989 | Sondal | ... | 215/230 |
| 4,873,193 A * | 10/1989 | Jensen et al. | ... | 436/176 |
| 4,919,286 A * | 4/1990 | Agbay, Sr. | ... | 215/235 |
| 5,076,453 A * | 12/1991 | Odet | ... | 215/252 |
| 5,092,478 A * | 3/1992 | La Pierre | ... | 215/256 |
| 5,207,783 A * | 5/1993 | Burton | ... | 215/256 |
| 5,249,695 A * | 10/1993 | Luch et al. | ... | 220/276 |
| 5,348,183 A * | 9/1994 | Luch et al. | ... | 220/265 |
| 5,456,375 A * | 10/1995 | May | ... | 215/252 |
| 5,465,876 A * | 11/1995 | Crisci | ... | 222/153.1 |
| 5,512,228 A * | 4/1996 | Adams et al. | ... | 264/152 |
| 5,547,092 A * | 8/1996 | Thompson | ... | 215/252 |
| 5,564,582 A * | 10/1996 | Kamath | ... | 215/252 |
| 5,678,714 A * | 10/1997 | Guglielmini | ... | 215/252 |
| 5,711,441 A * | 1/1998 | Adams et al. | ... | 215/48 |
| 5,711,443 A * | 1/1998 | Bennett | ... | 215/256 |
| 5,720,402 A * | 2/1998 | May | ... | 215/252 |
| 5,725,115 A * | 3/1998 | Bosl et al. | ... | 215/256 |
| 5,740,933 A * | 4/1998 | Conti et al. | ... | 215/256 |
| 5,785,209 A * | 7/1998 | Guglielmini | ... | 222/153.07 |
| 5,862,953 A * | 1/1999 | Long, Jr. | ... | 222/153.06 |
| 6,024,256 A * | 2/2000 | Beck et al. | ... | 222/153.06 |
| 6,029,834 A * | 2/2000 | Sanner | ... | 215/215 |
| 6,039,196 A * | 3/2000 | Ekkert et al. | ... | 215/216 |
| 6,050,436 A * | 4/2000 | Bennett et al. | ... | 215/256 |
| 6,253,939 B1 * | 7/2001 | Wan et al. | ... | 215/252 |
| 6,283,317 B1 * | 9/2001 | Benoit-gonin et al. | ... | 215/235 |
| 6,332,550 B1 * | 12/2001 | Bennett et al. | ... | 215/256 |
| 6,769,575 B1 * | 8/2004 | Long, Jr. | ... | 222/153.06 |
| 7,243,807 B2 * | 7/2007 | Lin | ... | 215/235 |
| 2005/0023238 A1 * | 2/2005 | Wong | ... | 215/252 |
| 2005/0092751 A1 * | 5/2005 | Alvares et al. | ... | 220/270 |
| 2005/0173367 A1 * | 8/2005 | Nusbaum et al. | ... | 215/237 |
| 2007/0023380 A1 * | 2/2007 | Shingle et al. | ... | 215/217 |

FOREIGN PATENT DOCUMENTS

| | | |
|---|---|---|
| GB | 2129784 A | 5/1984 |
| GB | 2312423 A | 10/1997 |
| WO | WO00/34141 | 2/1998 |
| WO | WO03/066467 | 8/2003 |
| WO | WO 03074381 A1 * | 9/2003 |

* cited by examiner

CONTAINER WITH LID AND TAMPER-EVIDENT FEATURES

TECHNICAL FIELD

The present invention relates to apparatus for secure sample collection, and also to apparatus for secure sample storage having a novel tamper-evident feature.

BACKGROUND ART

Over the last century, it has become desirable to be able to check vessels containing fluid, powder, solid and other compounds for evidence of tampering before the end user opens the vessel. This ensures a proof of quality and purity for the end user who can be assured that the product is delivered from the manufacturing supplier free of tampering by third parties.

It has become more evident that some samples, for example those used in forensic applications, need to be assured in more than one direction. Hence, there is a need to be able to supply an end user with a sealed vessel which has visibly not been tampered with by a third party en route to the end user, and for that end user to then be able to send the vessel onwards with a tamper-evident security feature that allows the recipient to see that tampering has been inhibited. The use of re-usable closures or seals obviously carries the risk that an interloper might remove the closure, tamper with the contents of the container, and reseal the container using the re-sealable closure without arousing the suspicions of the end user.

U.S. Pat. No. 5,720,402 discloses a container and a tamper-evident cap which fits the container in at least two closure positions. The tamper-evident cap has first and second bands, and the container has an annular slot for trapping the first band when the cap is in the first closure position and for trapping the second band when the cap is in the second closure position. The first band is retained in the annular slot when the cap is removed from the container, but must itself be removed before the annular slot can accommodate the second band. A pull tab is provided in the first band to allow its removal. The present applicant believes the discarded band may be problematic.

DISCLOSURE OF INVENTION

In accordance with a first aspect of the present invention, there is provided apparatus for securing sample collection, comprising: an open-topped container; a lid for securely covering the open-topped container to prevent access to container contents; and first and second tamper-evident features each having a frangible portion which fractures in use to provide an indication of tampering with the container contents when its respective tamper-evident feature is activated, with the first and second tamper-evident features being independently operable, and with activation of the first tamper-evident feature preventing activation of the second tamper-evident feature until the frangible portion of the first tamper-evident feature is fractured, wherein the second tamper evident feature is operable without having to remove the fractured frangible portion of the first tamper evident feature from the apparatus.

In this way, the first tamper-evident feature may be activated when despatching the sealed container to the end user. Upon receipt, the end user checks the integrity of the first tamper-evident feature. If intact, the end user breaks the first tamper-evident feature in order to gain internal access to the container and place a sample therein. Advantageously, the fractured frangible portion of the first tamper evident feature may be retained on the apparatus, thereby avoiding a waste disposal issue. If, on the other hand, the first tamper-evident feature is already broken when first received by the end user, the apparatus should not be used on the suspicion that tampering may have occurred. Once the sample is inside the container, the end user activates the second tamper-evident feature before dispatching the sample in the apparatus to the end recipient. Upon receipt, the end recipient checks the integrity of the second tamper-evident feature. If intact, the end recipient may break the second tamper-evident feature to remove the sample in the knowledge that third party access to the sample through removal of the lid has been denied. Advantageously, the fractured frangible portion of the second tamper evident feature may be retained on the apparatus, thereby avoiding a further waste disposal issue. The first tamper evident feature may even be retained as part of the apparatus after the frangible portions of the first and second tamper-evident features are fractured. Of course, if the second tamper-evident feature is broken when first received by the end recipient, foul play may be suspected.

At least one tamper-evident feature may be mounted on the lid, at least prior to fracture of its frangible portion. Indeed, both tamper-evident features may be mounted on, or at least associated with, the lid, at least prior to fracture of their respective frangible portions. The or each tamper-evident feature may be integrally formed with the lid, e.g. by injection moulding of plastics material. In this way, both the frangible portions of the first and second tamper-evident features may be retained on the container, again avoiding a waste disposal issue.

The lid and the open-topped container may have complementary screw threads for screwing the lid in an axial direction into mating engagement with the open-topped container when covering the same. The lid may have a central axis, and the first and second tamper-evident features may be axially offset relative to each other. For example, the frangible portion of the second tamper-evident feature may be disposed between the frangible portion of the first tamper-evident feature and the screw thread of the lid when covering the open-topped enclosure and the first tamper-evident feature is activated.

The frangible portion of the first tamper-evident feature may comprise a collar and frangible members coupling the collar to a body part (e.g. the second tamper-evident feature or the lid), with fracture of the frangible members releasing the collar from the body part. The collar may have a profile configured to engage a corresponding profile (e.g. of the open-topped container) including a protuberant step when the lid covers the open-topped container and the first tamper-evident feature is activated, with the collar being a friction fit over the protuberant step and a snug fit within an adjacent groove or recess to one side of the protuberant step. In this way, the collar may become trapped within the adjacent groove, facilitating fracture of the frangible members when the lid and open-topped container are separated for the first time after activation of the first tamper-evident feature. When released from the body part, the collar may be retained within the adjacent groove, providing a visible indication that the first tamper-evident feature has been broken. This may prevent easy use of a replacement first tamper-evident feature to disguise tampering.

The frangible portion of the second tamper-evident feature may comprise its own collar and frangible members coupling the collar to a rigid part (e.g. the lid), with fracture of the frangible members releasing the collar from the rigid part. The collar of the second tamper-evident feature may have a profile configured to engage a corresponding profile (e.g. of the open-topped container) including a further protuberant step when the lid covers the open-topped container and the second tamper-evident feature is activated, with the collar being a friction fit over the further protuberant step and a snug fit within an adjacent groove or recess. As with the collar of the first tamper-evident feature, the collar of the second tamper-evident feature may become trapped and retained within its respective groove once its frangible members are fractured.

The collar of the frangible portion of one tamper-evident feature may be configured to fit over the collar of the frangible portion of the other tamper-evident feature when one collar is released by fracture of its frangible members. For example, the collar of the first tamper-evident feature may fit over the collar of the second tamper-evident feature. In this way, the latter may at least in part become nested within the former when activating the second tamper-evident feature. Such an arrangement helps to prevent the collar of the first tamper-evident feature hindering activation of the second tamper-evident feature. It may also hinder any attempt to tamper with the second tamper-evident feature when activated.

A leading surface of at least one protuberant step may be angled to guide sliding movement thereover of its friction fitting collar when activating its respective tamper-evident feature. For example, the leading surface may have a profile corresponding to a curved outer surface of a frusto-conical body. At least one collar may include on its inner periphery a plurality of inwardly projecting lugs for providing a positive locating action in its intended groove when registered therewith. For example, the plurality of inwardly projecting lugs may be evenly spaced around the inner periphery of the collar. The lugs may be elongate and aligned end to end to form a discontinuous band or faceted ring around the inner periphery of the at least one collar. One lateral side of each elongate lug may be angled to guide sliding movement over the protuberant step with which it is a friction fit. An opposite lateral side of each elongate lug may be stepped for snagging engagement in its intended groove. The or each elongate lug may taper in at least one direction along its length. In this way, a sharp transition from lug to inner periphery of the collar may be avoided at one or both longitudinal ends of each lug. The absence of such a sharp transition may assist sliding movement of the lugs over the protuberant step with which they are a friction fit.

In accordance with a second aspect of the present invention, there is provided apparatus for secure sample storage, comprising: a first part defining an open-topped container; a second part defining a lid for securely covering the open-topped container; and a tamper-evident feature comprising a collar mounted by frangible members to one part, with fracture of the frangible members providing an indication of tampering with container contents once the tamper-evident feature is activated, the collar having a plurality of projecting lugs for engaging one side of a stepped profile in the other part when the tamper-evident feature is first activated, wherein the lugs are elongate and aligned end to end to form a band.

With such an arrangement, the direction of alignment of the elongate lugs may give rise to a positive locating action when engaging the one side of the stepped profile, and may even be accompanied by an audible "click" to provide additional reassurance of activation of the tamper-evident feature.

The tamper-evident feature may be mounted by the frangible members to the second part. In this way, the tamper-evident feature may be integrally formed with the lid. The elongate lugs may have spaces therebetween, thereby forming a discontinuous band. The lugs may project from an inner peripheral surface of the collar.

One lateral side of each elongate lug may be angled to ease sliding movement over the stepped profile. An opposite lateral side of each elongate lug may be stepped for snagging engagement with the one side of the stepped profile.

Each elongate lug may taper in at least one direction along its length. In this way, a sharp transition from lug to inner periphery of the collar may be avoided at one or both longitudinal ends of each elongate lug.

BRIEF DESCRIPTION OF DRAWINGS

An embodiment of the invention will now be described by way of example with reference to the following Figures, in which.

DESCRIPTION OF EMBODIMENT OF INVENTION

Figure 1:
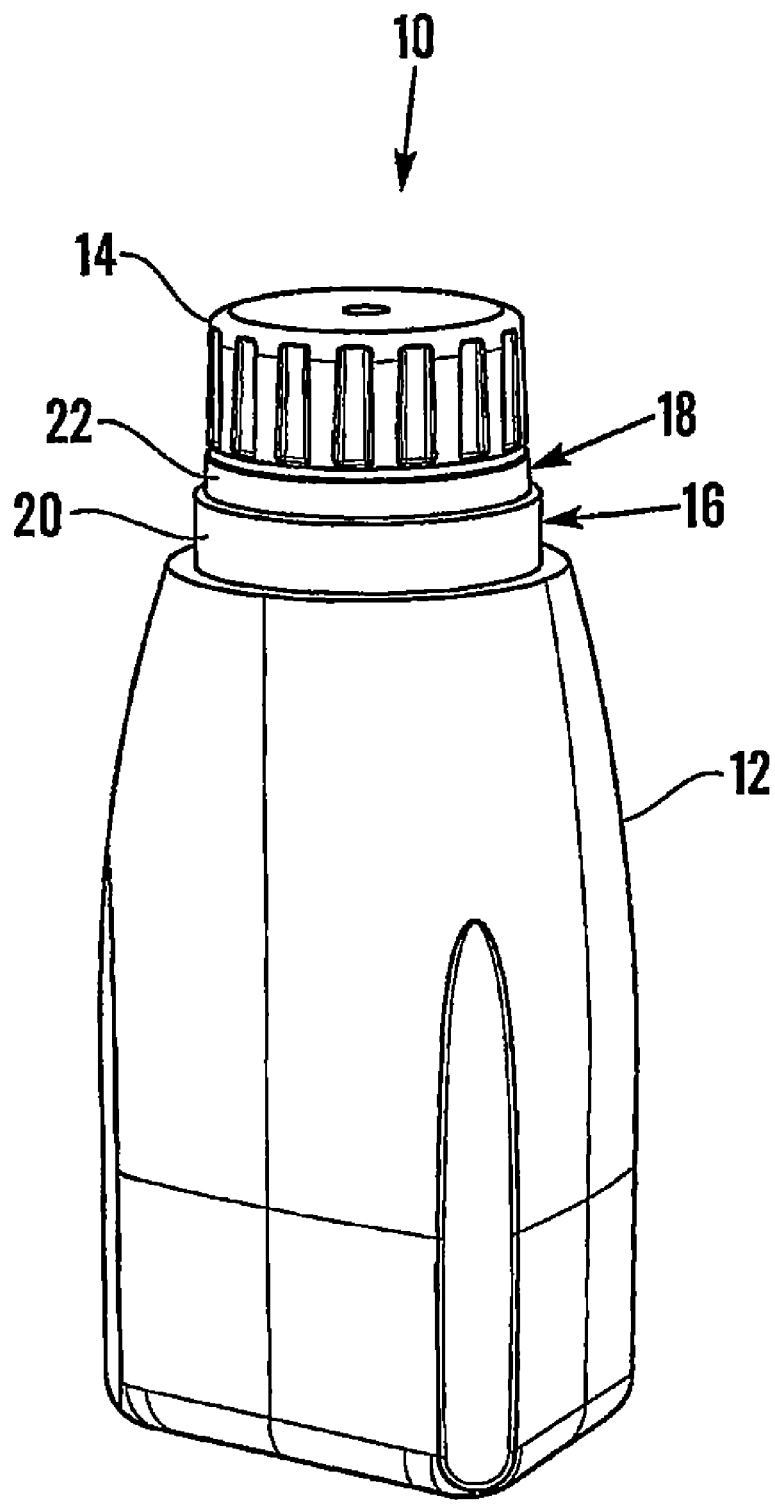
FIG. 1 is a perspective view of apparatus embodying the present invention.

FIG. 1 shows apparatus 10 embodying the present invention, and comprising an open-topped container 12 covered with a lid 14 to prevent access to container contents. The lid 14 includes first and second tamper-evident features 16,18 including respective first and second frangible portions 20,22, which fracture in use to provide an indication of tampering. The first and second tamper-evident features 16,18 are independently operable, with the first frangible portion 20 depending from the second frangible portion 22. The first tamper-evident feature 16 is configured to prevent activation of the second tamper-evident feature 18 until the frangible portion 20 is fractured.

Figure 2:
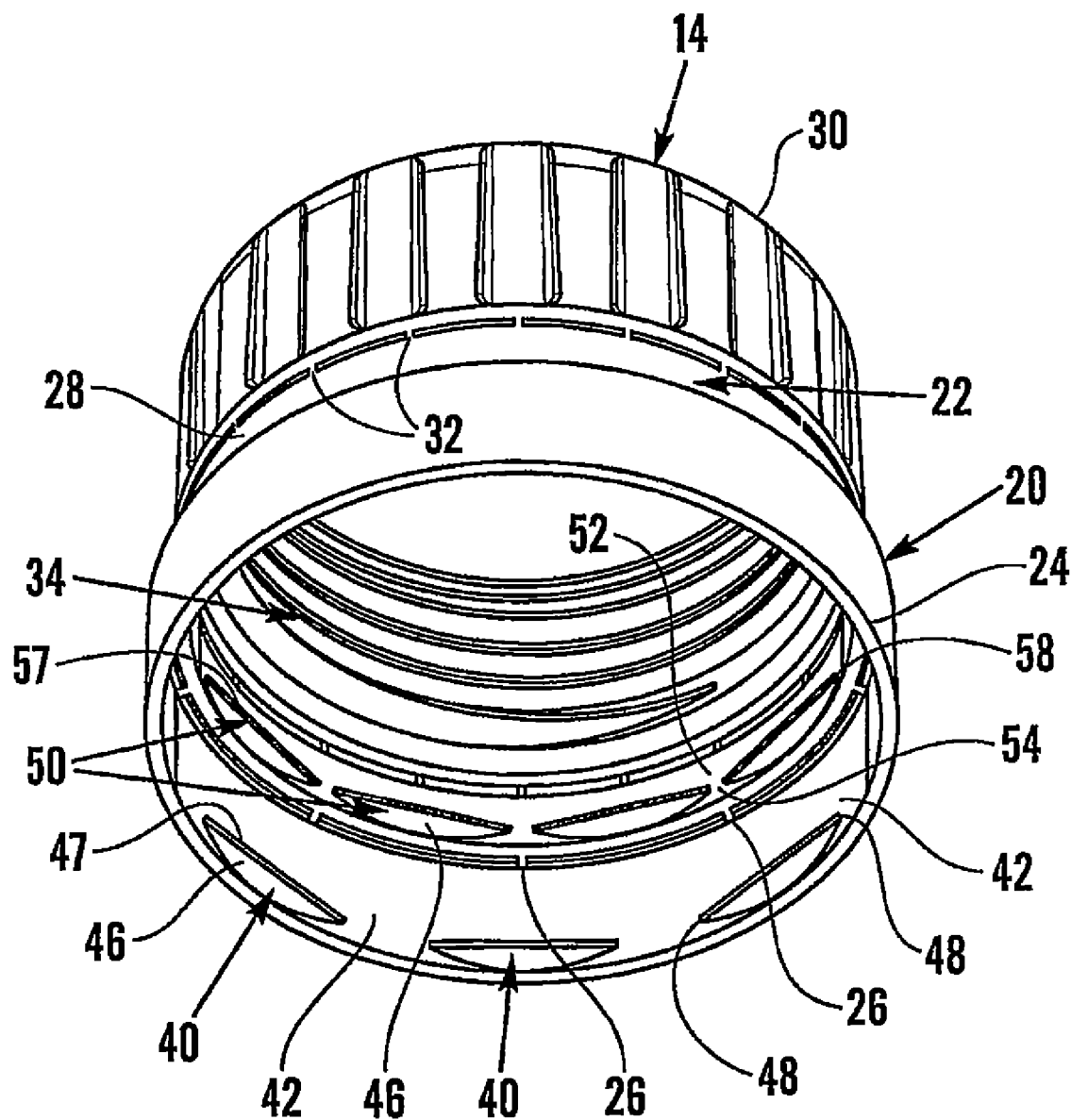
FIG. 2 is a perspective view showing lid detail of the apparatus of FIG. 1.

As shown in FIG. 2, the first frangible portion 20 comprises a first annular collar 24 mounted to the second frangible portion 22 by first frangible members or tabs 26. The first annular collar 24 is tear resistant so that it may remain intact when detached from the second frangible portion 22. The second frangible portion 22 comprises a second annular collar 28 mounted to the body 30 of lid 14 by second frangible members or tabs 32. The second annular collar 28 is also tear resistant. At least part of the second annular collar 28 is configured to fit or nest within the annular collar 24 when the latter becomes detached from the former. The body 30 has a screw thread 34.

The first annular collar 24 has a plurality of first elongate lugs 40 on its inner peripheral surface 42. The first elongate lugs 40 are aligned end to end with spaces 44 therebetween to form a first discontinuous ring. Similarly, the second annular collar 28 has a plurality of second elongate lugs 50 on its inner periphery 52. The second elongate lugs 50 are aligned end to end with spaces 54 therebetween to form a second discontinuous ring. The function of the first and second discontinuous rings will be described later. Each elongate lug 40,50 has on one lateral side a ramp profile 46,56 respectively and a sharp stepped profile 47,57 on the other lateral side. In addition, the longitudinal ends 48,58 of each elongate lug taper towards the inner periphery 42,52 of its respective collar 24,28, so that there is a smooth transition from lug to collar periphery around the discontinuous rings.

Figure 3:
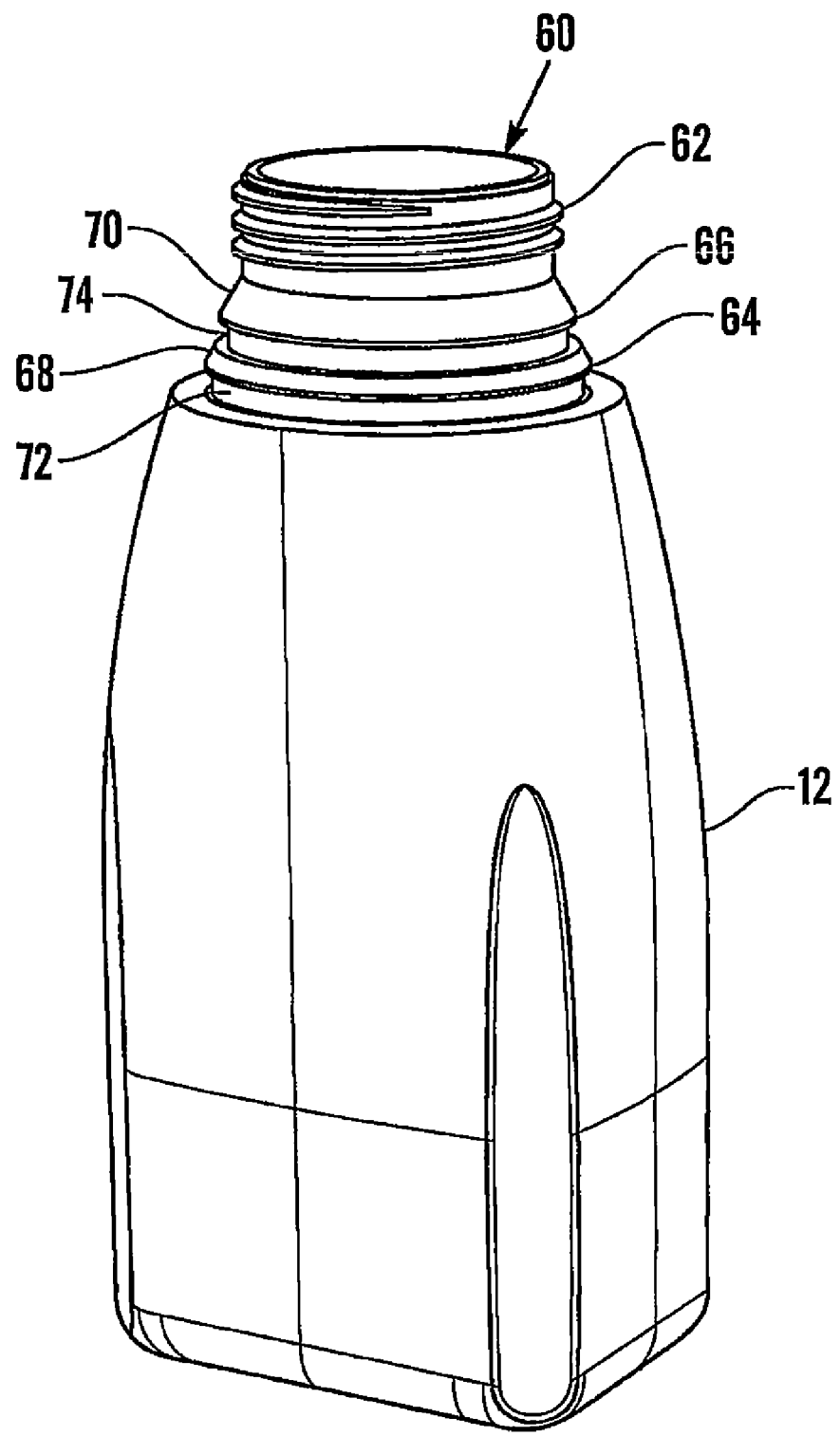
FIG. 3 shows container detail of the apparatus of FIG. 1.
Figure 4:
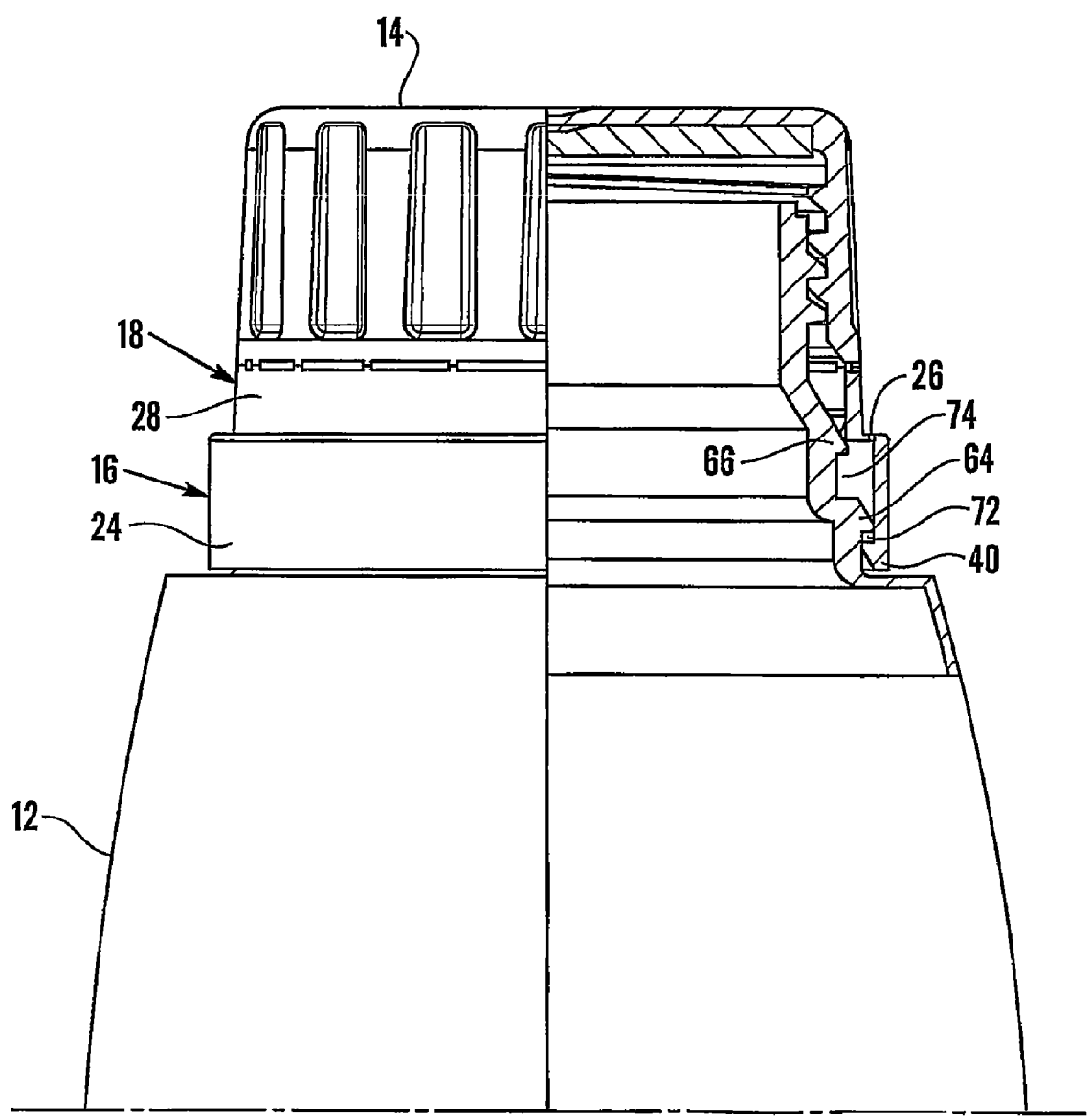
FIG. 4 is a partial cut-away schematic view showing activation of a first tamper-evident feature in the apparatus of FIG. 1.
Figure 5:
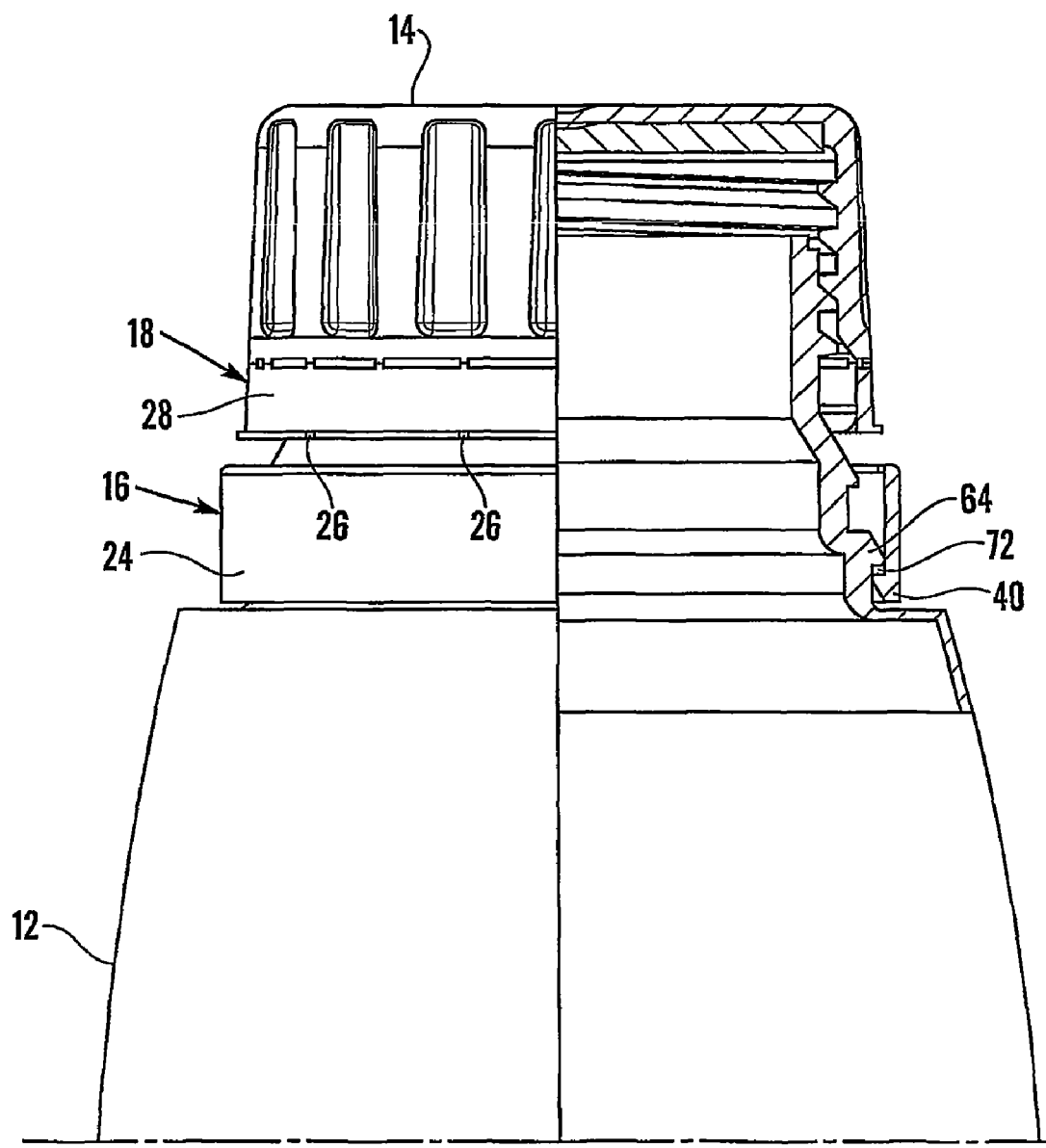
FIG. 5 shows a partial cut-away schematic view illustrating fracture of the first tamper-evident feature activated in FIG. 4.

As shown in FIG. 3, the open-topped container 12 has a neck 60 with a screw thread 62 for threadably engaging the screw thread 34 of the body 30 of lid 14. The neck 60 includes a first and a second protuberant step profiles 64, 66. Each step profile 64, 66 has a respective leading surface 68, 70 having a profile corresponding to a curved outer surface of a frusto-conical body, and a respective trailing surfaced defining a respective recess 72, 74.

The first and second protuberant step profiles 64,66 are part of the first and second tamper-evident features 16,18. The first annular collar 24 is a loose fit over the second protuberant step profile 66, but a friction fit over the first protuberant step profile 64. The second annular collar 28 is a friction fit over the second protuberant step profile 66. Furthermore, the first and second protuberant step profiles 64,66 are axially spaced such that second tamper evident feature 18 is not activated during activation of the first tamper-evident feature 16.

The use of the apparatus 10 will now be described with reference to FIGS. 4 to 7. The first tamper-evident feature 16 is activated by screwing the lid 14 onto the open-topped container 12 until the elongate lugs 40 pass over the first protuberant step profile 64 and snaggingly engage the recess 72 when registered therewith. In this condition, the apparatus 10 may be despatched to an end user. Upon receipt, the end user unscrews the lid 14 to open the container 12. In doing so, the first annular collar 24 is retained by the first protuberant step profile 64, which causes first frangible members 26 to fracture. The first annular collar 24 is thus left behind on the neck 60 of open-topped container 12 as the lid 14 is removed.

Figure 6:
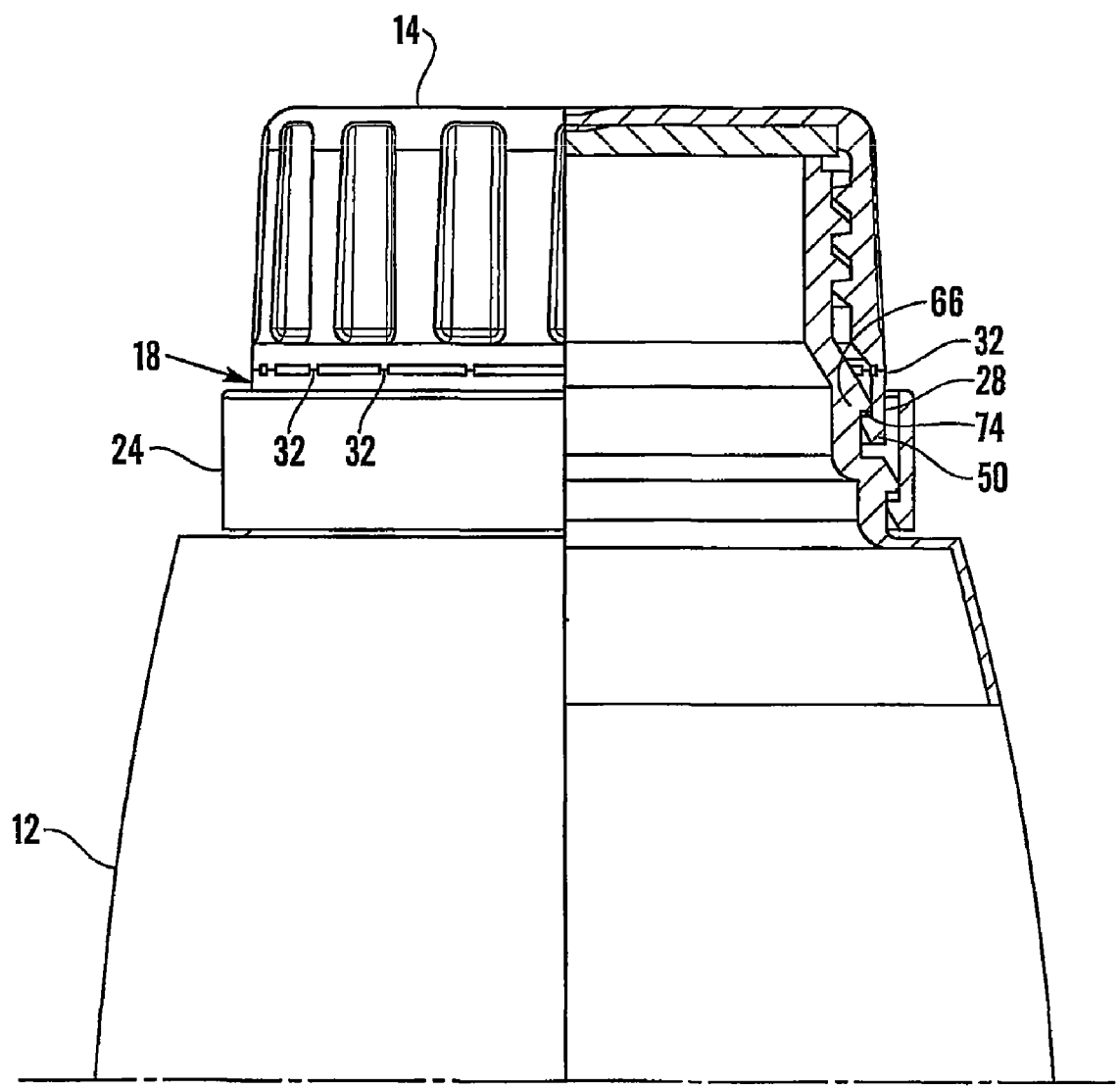
FIG. 6 shows a partial cut-away schematic view showing activation of a second tamper-evident feature of the apparatus for FIG. 1.
Figure 7:
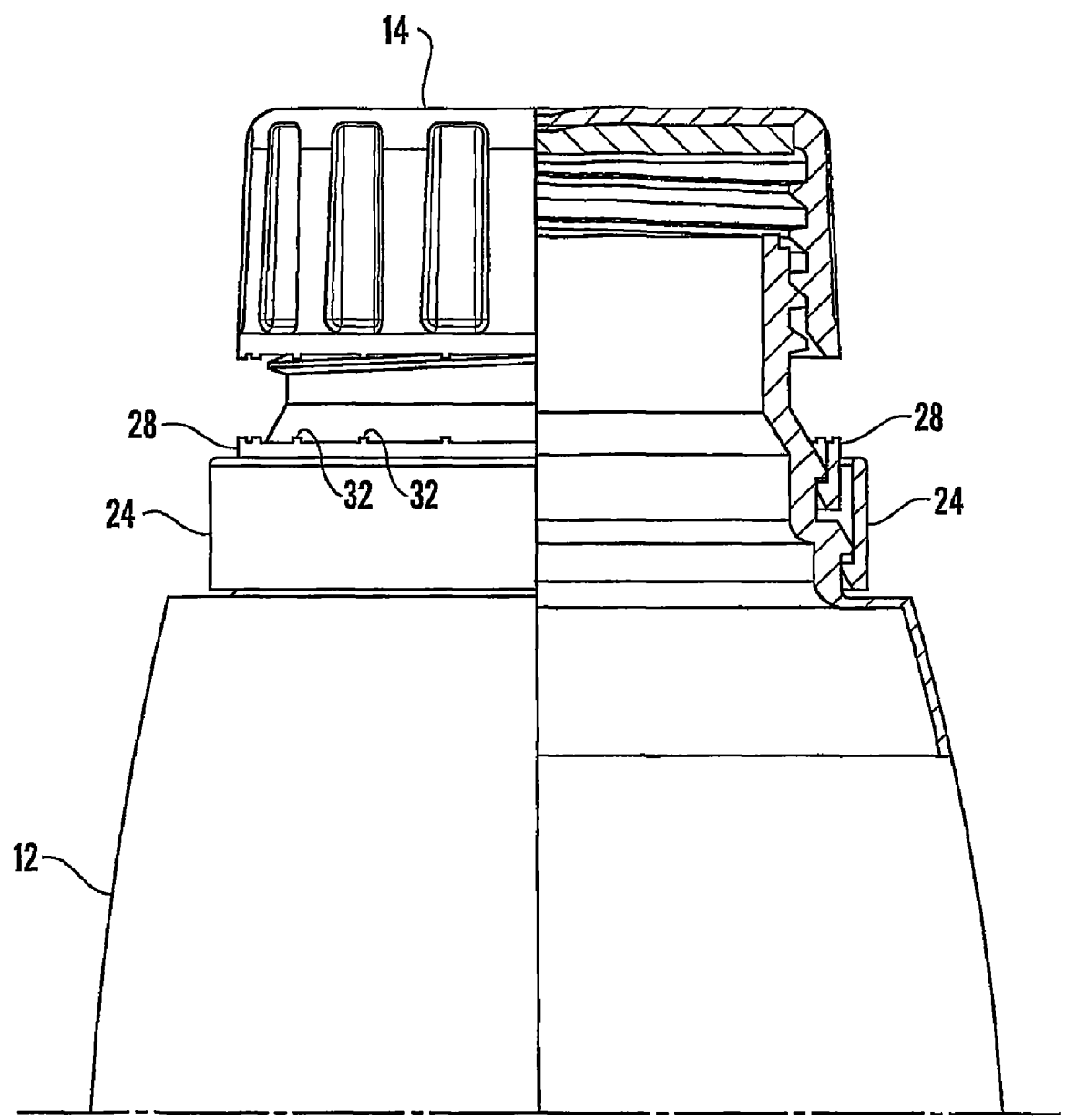
FIG. 7 shows a partial cut-away schematic view illustrating fracture of the second tamper-evident feature of FIG. 6.

Once the end user has put a sample in the open-topped container 12, the lid 14 is screwed back on to activate the second tamper-evident feature 18. As shown in FIG. 6, the lid 12 is screwed down tight to bring the elongate lugs 50 over the second protuberant step profile 66 and into snagging engagement with the recess 74 when registered therewith. It will be noted that second annular collar 28 is now partially nested within the first annular collar 24.

In this condition, the apparatus 10 (complete with sample) may be despatched to an end recipient. Upon receipt, the end recipient unscrews the lid 14 from the container 14 to gain access to the sample. In doing so, the second annular collar 28 is retained by the second protuberant step profile 66, which causes second frangible members 32 to fracture. The second annular collar 28 is thus left behind on the neck 60 of open-topped container 12 as the lid 14 is removed.

The invention claimed is:

1. An apparatus for securing sample collection, comprising:
   an open-topped container having a neck, the neck comprising a first protuberant step and a second protuberant step;
   a lid for securely covering the open-topped container to prevent access to container contents, the lid comprising:
   a first tamper-evident feature having a first frangible portion and a first plurality of lugs; and
   a second tamper-evident feature having a second frangible portion and a second plurality of lugs;
   wherein the first frangible portion and second frangible portion fracture in use to provide an indication of tampering with container contents when its respective tamper-evident feature is activated, with the first tamper-evident feature and second tamper-evident feature being independently fractured and activated from one another; and,
   wherein a first of the first tamper-evident feature occurs when the first plurality of lugs engages the first protuberant step and a second activation of the second tamper-evident feature occurs when the second plurality of lugs engages the second protuberant step, wherein the first activation of the first tamper-evident feature prevents the second activation of the second tamper-evident feature until the first frangible portion is fractured, wherein the second tamper-evident feature is activated and then fractured without having to remove the fractured frangible portion of the first tamper-evident feature from the apparatus.

2. Apparatus according to claim 1, wherein the lid and the open-topped container have complementary screw threads for screwing the lid in an axial direction into mating engagement with the open-topped container when covering the same.

3. Apparatus according to claim 1, wherein the plurality of inwardly projecting lugs are evenly spaced around the inner periphery of the collar.

4. Apparatus according to claim 1, wherein the first and second tamper-evident features are axially offset relative to each other.

5. Apparatus according to claim 4, wherein the second frangible portion of the second tamper-evident feature is disposed between the first frangible portion of the first tamper-evident feature and the screw thread of the lid when covering the open-topped enclosure and the first tamper-evident feature is activated.

6. Apparatus according to claim 1, wherein at least one of the tamper-evident features is mounted on the lid, at least prior to fracture of its frangible portion.

7. Apparatus according to claim 6, wherein both tamper-evident features are mounted on, or at least associated with, the lid, at least prior to fracture of their respective frangible portions.

8. Apparatus according to claim 6 wherein the at least one of the tamper-evident features is integrally formed with the lid.

9. Apparatus according to claim 1, wherein the lugs are elongate and aligned end to end to form one of a discontinuous band and faceted ring around the inner periphery of the at least one collar.

10. Apparatus according to claim 9, wherein one lateral side of each elongate lug is angled to guide sliding movement over the protuberant step with which it is a friction fit.

11. Apparatus according to claim 10, wherein an opposite lateral side of each elongate lug is stepped for snagging engagement in its intended groove.

12. Apparatus according to claim 9, wherein the or each elongate lug tapers in at least one direction along its length.

13. Apparatus according to claim 1, wherein the first frangible portion of the first tamper-evident feature further comprises a collar that includes the lugs and frangible members coupling the collar to a body part, with fracture of the frangible members releasing the collar from the body part.

14. Apparatus according to claim 13, wherein the body part is one of one of the second tamper-evident feature and the lid.

15. Apparatus according to claim 13, wherein the collar is configured to engage the first protuberant step when the lid covers the open-topped container and the first tamper-evident feature is activated, with the collar being a friction fit over the first protuberant step and a snug fit within an adjacent groove or recess to one side of the first protuberant step.

16. Apparatus according to claim 15, wherein a leading surface of at least one of the first or the second protuberant steps is angled to guide sliding movement thereover of its friction fitting.

17. Apparatus according to claim 16, wherein the leading surface has a profile corresponding to a curved outer surface of a frusto-conical body.

18. Apparatus according to claim 15, wherein the corresponding profile is part of the open-topped container.

19. Apparatus according to claim 13, wherein the second frangible portion of the second tamper-evident feature comprises a collar having the second plurality of lugs and frangible members coupling the collar to a rigid part with fracture of the frangible members releasing the collar from the rigid part.

20. Apparatus according to claim 19, wherein the rigid part is the lid.

21. Apparatus according to claim 19, wherein the collar of the second tamper-evident feature is configured to engage the second protuberant step when the lid covers the open-topped container and the second tamper-evident feature is activated, with the collar being a friction fit over the second protuberant step and a snug fit within an adjacent groove or recess.

22. Apparatus according to claim 21, wherein the respective corresponding profile is part of the open-topped container.

23. Apparatus according to claim 19, wherein the collar of the first tamper-evident feature is configured to fit over the collar of the second tamper-evident feature when the first collar is released by fracture of its frangible members.

24. Apparatus according to claim 23, wherein the collar of the first tamper-evident feature fits over the collar of the second tamper-evident feature.

* * * * *